United States Patent
Lorman et al.

[11] Patent Number: 5,853,672
[45] Date of Patent: Dec. 29, 1998

[54] AUTOMOBILE AIR FRESHNER DISPENSING SYSTEM

[76] Inventors: Mikhail Lorman; Osker Purer, both of 5714 Old Sunrise Hwy., Massapequa, N.Y. 11758

[21] Appl. No.: 749,519

[22] Filed: Nov. 18, 1996

[51] Int. Cl.[6] ................................................ A61L 9/12
[52] U.S. Cl. ............................ 422/124; 422/5; 422/306; 239/211
[58] Field of Search ................................ 422/5, 120, 306, 422/122, 123, 124; 424/76.1; 239/211, 71, 326, 145; 280/727

[56] References Cited

U.S. PATENT DOCUMENTS

| | | | |
|---|---|---|---|
| 3,410,488 | 11/1968 | Sugimura | 239/55 |
| 3,722,182 | 3/1973 | Gilbertson | 96/52 |
| 3,990,848 | 11/1976 | Corris | 422/49 |
| 4,523,870 | 6/1985 | Spector | 454/157 |
| 4,814,212 | 3/1989 | Spector | 428/14 |
| 4,916,584 | 4/1990 | Gustafson | 362/503 |
| 5,071,621 | 12/1991 | Tokuhiro et al. | 422/4 |
| 5,233,680 | 8/1993 | Fussell | 392/390 |
| 5,334,361 | 8/1994 | Rafaelides et al. | 422/305 |
| 5,460,787 | 10/1995 | Colon | 422/123 |
| 5,562,407 | 10/1996 | Cielo | 415/121.2 |

*Primary Examiner*—Mary E. Mosher

[57] ABSTRACT

A new Automobile Air Freshener Dispensing System for radiating a pleasant scent into a vehicle and activating decorative lights whenever a driver presses upon a brake pedal, thereby reducing the concentration of the scent within the vehicle and extending the life of the scenting material. The inventive device includes an encasement having an interior cavity, a plurality of lights secured around an exterior perimeter of the encasement and electrically coupled to a brake light control switch, a fan positioned within the interior cavity and electrically coupled in parallel to the lights, and a replaceable aroma filter positioned juxtaposed to the fan by a vent cover.

13 Claims, 3 Drawing Sheets

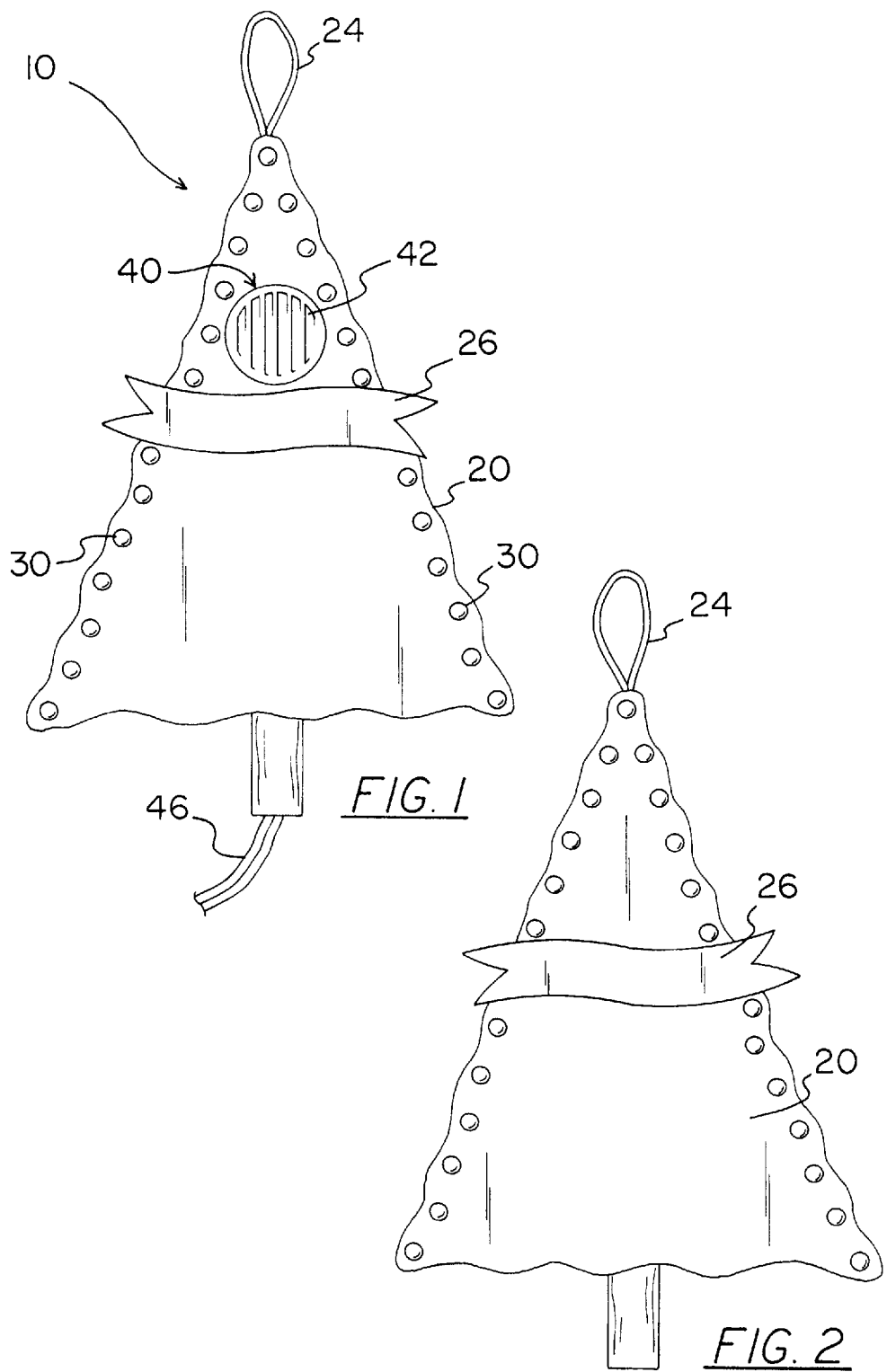

AUTOMOBILE AIR FRESHNER DISPENSING SYSTEM

BACKGROUND OF THE INVENTION

1. Field of the Invention

The present invention relates to Air Freshening Devices and more particularly pertains to a new Automobile Air Freshener Dispensing System for radiating pleasant scent into a vehicle and activating decorative lights whenever a driver presses upon a brake pedal, thereby reducing the concentration of the scent within the vehicle and extending the life of the scenting material.

2. Description of the Prior Art

The use of Air Freshening Devices is known in the prior art. More specifically, Air Freshening Devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art Air Freshening Devices include U.S. Pat. No. 5,334,361; U.S. Pat. No. 4,814,212; U.S. Design Pat. No. 359,347; U.S. Design Pat. No. 280,014; U.S. Pat. No. 4,197,271 and U.S. Design Pat. No. 356,373.

While these devices fulfill their respective, particular objectives and requirements, the aforementioned patents do not disclose a new Automobile Air Freshener Dispensing System. The inventive device includes an encasement having an interior cavity, a plurality of lights secured around an exterior perimeter of the encasement and electrically coupled to a brake light control switch, a fan positioned within the interior cavity and electrically coupled in parallel to the lights, and a replaceable aroma filter positioned juxtaposed to the fan by a vent cover.

In these respects, the Automobile Air Freshener Dispensing System according to the present invention substantially departs from the conventional concepts and designs of the prior art, and in so doing provides an apparatus primarily developed for the purpose of radiating a pleasant scent into a vehicle and activating decorative lights whenever a driver presses upon a brake pedal, thereby reducing the concentration of the scent within the vehicle and extending the life of the scenting material.

SUMMARY OF THE INVENTION

In view of the foregoing disadvantages inherent in the known types of Air Freshening Devices now present in the prior art, the present invention provides a new Automobile Air Freshener Dispensing System construction wherein the same can be utilized for radiating a pleasant scent into a vehicle and activating decorative lights whenever a driver presses upon a brake pedal, thereby reducing the concentration of the scent within the vehicle and extending the life of the scenting material.

The general purpose of the present invention, which will be described subsequently in greater detail, is to provide a new Automobile Air Freshener Dispensing System apparatus and method which has many of the advantages of the Air Freshening Devices mentioned heretofore and many novel features that result in a new Automobile Air Freshener Dispensing System which is not anticipated, rendered obvious, suggested, or even implied by any of the prior art Air Freshening Devices, either alone or in any combination thereof.

To attain this, the present invention generally comprises an encasement having an interior cavity, a plurality of lights secured around an exterior perimeter of the encasement and electrically coupled to a brake light control switch, a fan positioned within the interior cavity and electrically coupled in parallel to the lights, and a replaceable aroma filter positioned juxtaposed to the fan by a vent cover.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Automobile Air Freshener Dispensing System apparatus and method which has many of the advantages of the Air Freshening Devices mentioned heretofore and many novel features that result in a new Automobile Air Freshener Dispensing System which is not anticipated, rendered obvious, suggested, or even implied by any of the prior art Air Freshening Devices, either alone or in any combination thereof.

It is another object of the present invention to provide a new Automobile Air Freshener Dispensing System which may be easily and efficiently manufactured and marketed.

It is a further object of the present invention to provide a new Automobile Air Freshener Dispensing System which is of a durable and reliable construction.

An even further object of the present invention is to provide a new Automobile Air Freshener Dispensing System which is susceptible of a low cost of manufacture with regard to both materials and labor, and which accordingly is then susceptible of low prices of sale to the consuming public, thereby making such Automobile Air Freshener Dispensing System economically available to the buying public.

Still yet another object of the present invention is to provide a new Automobile Air Freshener Dispensing System which provides in the apparatuses and methods of the prior art some of the advantages thereof, while simultaneously overcoming some of the disadvantages normally associated therewith.

Still another object of the present invention is to provide a new Automobile Air Freshener Dispensing System for radiating a pleasant scent into a vehicle and activating decorative lights whenever a driver presses upon a brake pedal, thereby reducing the concentration of the scent within the vehicle and extending the life of the scenting material.

Yet another object of the present invention is to provide a new Automobile Air Freshener Dispensing System which includes an encasement having an interior cavity, a plurality of lights secured around an exterior perimeter of the encasement and electrically coupled to a brake light control switch, a fan positioned within the interior cavity and electrically coupled in parallel to the lights, and a replaceable aroma filter positioned juxtaposed to the fan by a vent cover.

Still yet another object of the present invention is to provide a new Automobile Air Freshener Dispensing System that extends the useful life of the aroma filter.

Even still another object of the present invention is to provide a new Automobile Air Freshener Dispensing System that allows various multiple aroma filters to be combined to create a selected scent.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a front view of a new Automobile Air Freshener Dispensing System according to the present invention.

FIG. 2 is a rear view of the present invention.

DESCRIPTION OF THE PREFERRED EMBODIMENT

Figure 3:
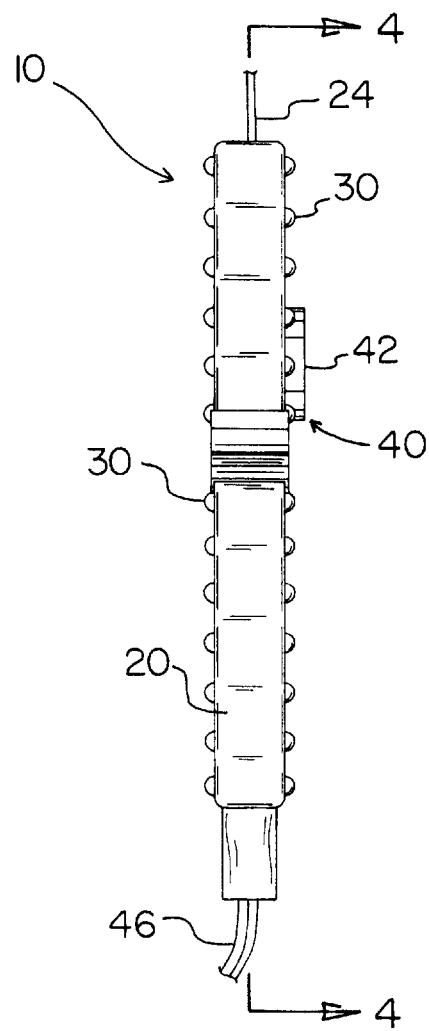
FIG. 3 is side view of the present invention.

With reference now to the drawings, and in particular to FIGS. 1 through 6 thereof, a new Automobile Air Freshener Dispensing System embodying the principles and concepts of the present invention and generally designated by the reference numeral 10 will be described.

More specifically, it will be noted that the Automobile Air Freshener Dispensing System 10 comprises an encasement 20 having an interior cavity 22, and a scent dispensing means 40 secured within the interior cavity 22 and electrically coupled to an unnumbered brake light switch of a vehicle, whereby the scent dispensing means 40 radiates various scents when the unnumbered brake light switch is closed.

Figure 4:
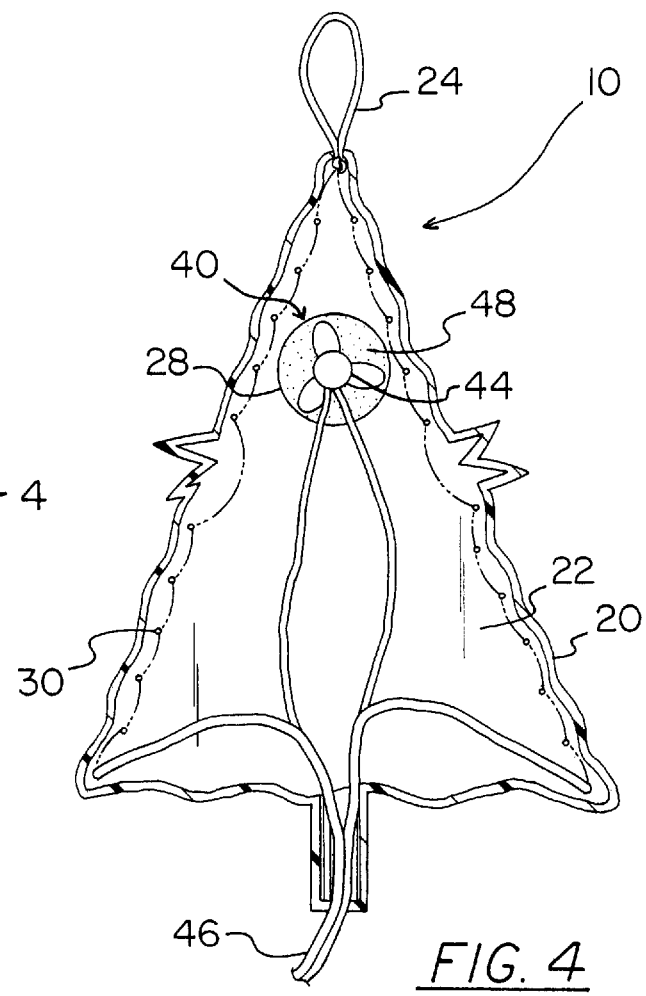
FIG. 4 is a cross sectional view taken along line 4—4 of FIG. 3.
Figure 5:
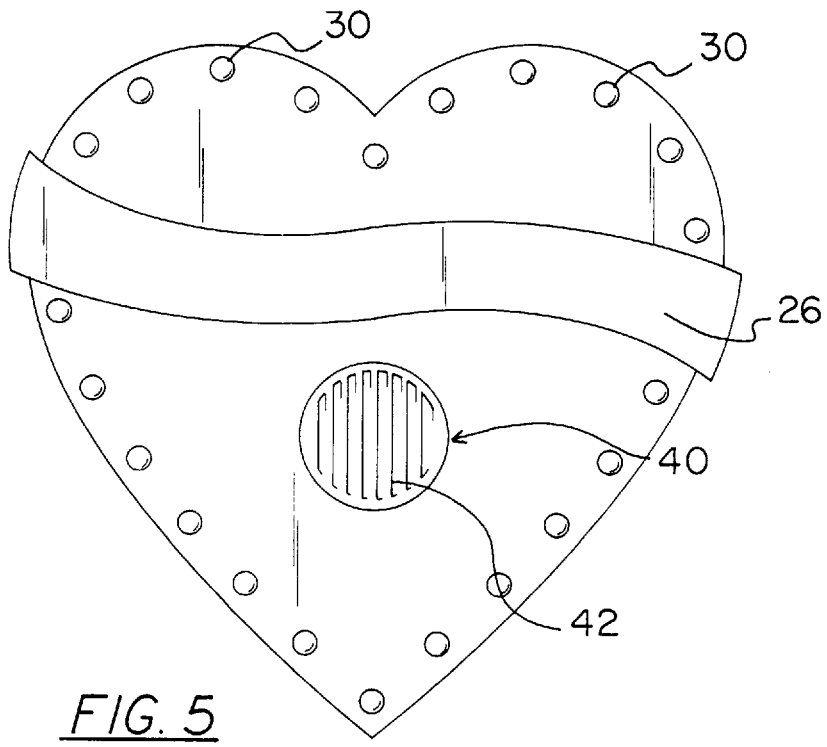
FIG. 5 is a front view of an alternative embodiment having a portable power source.

As best illustrated in FIGS. 1 through 4, it can be shown that the scent dispensing means 40 has a fan 44 secured within the interior cavity 22 of the encasement 20 juxtaposed to the plane of an aperture 28 into the encasement 20. The fan 44 is electrically coupled to the unnumbered brake light switch. At least one aroma filter 48, having a selected scent, is juxtaposed to the aperture 28 opposite of the fan 44. As shown in FIGS. 1 and 4, a vent cover 42 is removably coupled to the encasement 20 and surrounds the aperture 28 thereby retaining the aroma filter 48 juxtaposed to the aperture 28. As shown in FIGS. 1 through 5, preferably a plurality of lights 30 are secured to the encasement 20 near an exterior perimeter. The lights 30 are electrically coupled in parallel to the fan 44 as shown in FIG. 4. When the unnumbered brake light switch is closed the lights 30 radiate light simultaneously with the scent dispensing means 40. As shown in FIGS. 1 through 4, a loop 24 is secured to an upper end of the encasement 20 to allow positioning of the invention within the vehicle. The encasement 20 may be formed into a shape of a Christmas tree, as shown in FIGS. 1 through 4, or into a shape of a heart, as shown in FIGS. 5 and 6, with an indicia 26 secured to a front surface of the encasement 20.

Figure 6:
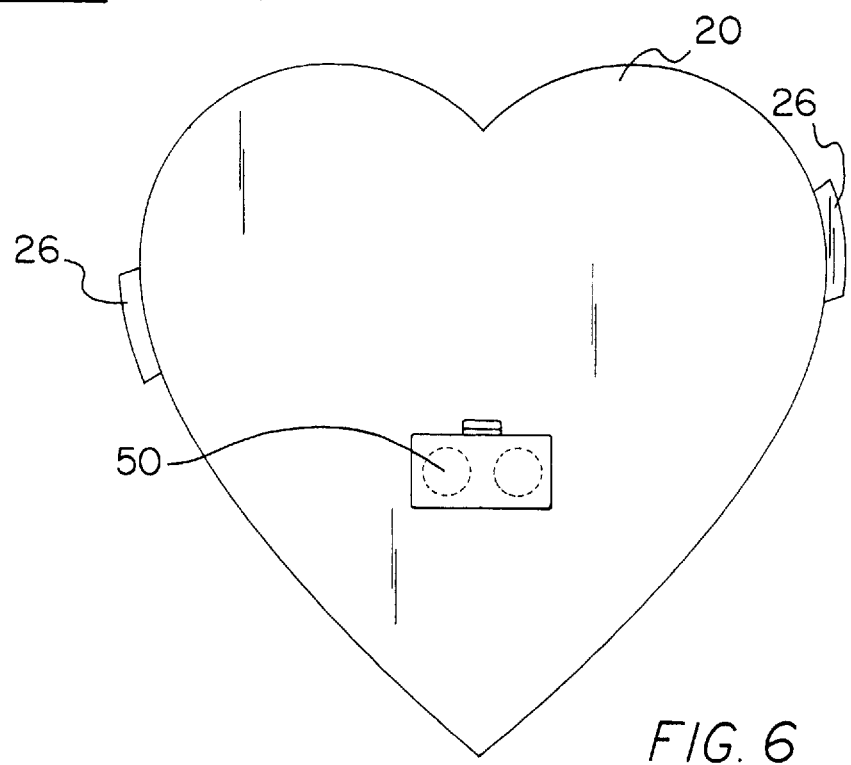
FIG. 6 is a rear view of the alternative embodiment.

In an alternative embodiment as shown in FIGS. 5 and 6, the unnumbered brake light switch is replaced with a portable power source 50 such as a battery. This allows utilization of the present invention in or outside of the vehicle, such as in an office or home.

In use, the driver of the vehicle presses a brake pedal thereby closing the unnumbered brake light switch. The fan 44 is electrically charged from the closing of the unnumbered brake light switch which causes rotation of the fan 44. The fan 44 propels air from within the interior cavity 22 through the aroma filter 48. The propelled air exits through the vent cover 42 with the scent from the aroma filter 48. The plurality of lights 30 are also electrically charged to radiate light which is decorative and can be utilized as a third brake light for the vehicle warning other drivers of the driver slowing down. This process of activating the fan 44 only during the stopping of the vehicle provides an extended life for the aroma filter 48 and prevents an excess concentration of the scent within the vehicle during non-use.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An automobile air freshener dispensing system comprising:

an encasement having an interior cavity; and a scent dispensing means for dispensing a scent into an area, said scent dispensing means being secured within said interior cavity, said scent dispensing means further being adapted for electrically coupling to a brake light switch of a vehicle such that said scent dispensing means is activated when the brake light switch is closed, whereby said scent dispensing means emits said scent when said brake light switch is closed;

said encasement being further structured to include an aperture;

said scent dispensing means including a fan secured within said interior cavity of said encasement, said fan being juxtaposed to said aperture, said fan further being electrically coupled to said brake light switch;

at least one aroma filter having a selected scent; and a vent cover, said vent cover being removably coupled to an outside of said encasement and surrounding said aperture;

wherein said aroma filter is positioned between said aperture and said vent cover such that said vent cover retains said aroma filter juxtaposed to said aperture.

2. The automobile air freshener dispensing system of claim 1, wherein a plurality of lights are secured to said encasement, said plurality of lights being positioned near an exterior perimeter of said encasement, said lights being electrically coupled in parallel to said fan, whereby said plurality of lights illuminate when said brake light switch is closed.

3. The automobile air freshener dispensing system of claim 1, wherein a loop is secured to an upper end of said encasement.

4. The automobile air freshener dispensing system of claim 1, wherein said encasement is formed into a shape of a Christmas tree.

5. The automobile air freshener dispensing system of claim 1, wherein said encasement is formed into a shape of a heart.

6. An air freshener dispensing system comprising:

an encasement having an interior cavity;

a scent dispensing means for dispensing a scent into an area, said scent dispensing means being secured within said interior cavity, said scent dispensing means further being adapted for electrically coupling to a portable power source;

said encasement being further structured to include an aperture;

said scent dispensing means including a fan secured within said interior cavity of said encasement, said fan being juxtaposed to said aperture, said fan further being electrically coupled to said portable power source;

at least one aroma filter having a selected scent;

a vent cover, said vent cover being removably coupled to an outside of said encasement and surrounding said aperture;

wherein said aroma filter is positioned between said aperture and said vent cover such that said vent cover retains said aroma filter juxtaposed to said aperture; and wherein a plurality of lights are secured to said encasement, said plurality of lights being positioned near an exterior perimeter of said encasement, said lights being electrically coupled in parallel to said fan, whereby said plurality of lights illuminate when said portable power source is activated.

7. The air freshener dispensing system of claim 6, wherein a loop is secured to an upper end of said encasement.

8. The air freshener dispensing system of claim 7, wherein said encasement is formed into a shape of a Christmas tree.

9. The air freshener dispensing system of claim 7, wherein said encasement is formed into a shape of a heart.

10. An automobile air freshener dispensing system for connection to a brake light circuit of a vehicle, the air freshener dispensing system comprising:

a housing being structured to have an interior, said housing further being structured to include an aperture in a forward face of said housing;

scent dispensing means positioned within said housing, said scent dispensing means being adapted for forcing air out from said interior through said aperture, said scent dispensing means being adapted for electrical connection to the brake light circuit of the vehicle such that said scent dispensing means is activated by closing of the brake light circuit;

an aroma filter having a selected scent;

a vent cover removably attached to said forward face of said housing around said aperture, said vent cover having a plurality of vents such that the air forced through said aperture by said scent dispensing means passes through said vents;

said aroma filter being positioned adjacent said aperture and between said forward face and said vent cover, whereby the air forced through said aperture by said scent dispensing means contacts said aroma filter and dispenses said selected scent through said vents; and a plurality of lights, said plurality of lights being adapted for electrical connection to the brake light circuit such that said plurality of lights illuminate when the brake light circuit is closed.

11. The automobile air freshener dispensing system of claim 10 wherein said plurality of lights are positioned proximate a perimeter edge of said forward face.

12. The automobile air freshener dispensing system of claim 10, wherein the housing has a shape chosen from the group of shapes consisting of a Christmas tree and a heart.

13. The automobile air freshener dispensing system of claim 12, wherein the housing has a shape chosen from the group of shapes consisting of a Christmas tree and a heart.

* * * * *